US 6,605,095 B2

(12) United States Patent
Grossman

(10) Patent No.: US 6,605,095 B2
(45) Date of Patent: Aug. 12, 2003

(54) PERCUTANEOUS NEEDLE ALIGNMENT SYSTEM AND ASSOCIATED METHOD

(75) Inventor: Jeffrey Grossman, Atlanta, GA (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/866,238

(22) Filed: May 25, 2001

(65) Prior Publication Data
US 2001/0053915 A1 Dec. 20, 2001

Related U.S. Application Data
(60) Provisional application No. 60/211,279, filed on Jun. 13, 2000, and provisional application No. 60/216,378, filed on Jul. 5, 2000.

(51) Int. Cl.$^7$ .............................................. A61B 19/00
(52) U.S. Cl. ...................................... 606/130; 356/399
(58) Field of Search .......................... 606/130; 356/399, 356/400

(56) References Cited

U.S. PATENT DOCUMENTS

| | | | |
|---|---|---|---|
| 3,582,214 A | | 6/1971 | Loomis |
| 3,801,205 A | * | 4/1974 | Eggenschwyler ........... 356/138 |
| 3,964,480 A | * | 6/1976 | Froning ...................... 604/117 |
| 4,000,948 A | | 1/1977 | Miller |
| 4,319,839 A | * | 3/1982 | Durran ....................... 356/153 |
| 4,638,799 A | * | 1/1987 | Moore ........................ 604/116 |
| 4,651,732 A | | 3/1987 | Frederick |
| 4,674,870 A | * | 6/1987 | Cain et al. .................. 356/4.08 |
| 5,320,111 A | * | 6/1994 | Livingston .................. 378/206 |
| 5,598,269 A | * | 1/1997 | Kitaevich et al. ........... 356/399 |
| 5,638,208 A | | 6/1997 | Walker |
| 5,810,841 A | | 9/1998 | McNeirney et al. |
| 5,838,882 A | | 11/1998 | Gan et al. |
| 5,973,788 A | | 10/1999 | Pettersen et al. |
| 5,991,043 A | * | 11/1999 | Andersson et al. ......... 356/400 |
| 6,021,343 A | | 2/2000 | Foley et al. |
| 6,041,249 A | | 3/2000 | Regn |
| 6,096,049 A | | 8/2000 | McNeirney et al. |
| 6,443,960 B1 | * | 9/2002 | Brabrand et al. ........... 600/427 |

FOREIGN PATENT DOCUMENTS

| | | | |
|---|---|---|---|
| FR | 2384481 | * 10/1978 | ............ A61B/6/08 |
| WO | WO 98/36688 A1 | 8/1998 | |

OTHER PUBLICATIONS

Stoianovici, Dan, "A Novel Mechanical Transmission Applied To Percutaneous Renal Access", University Paper, Baltimore, MD.

* cited by examiner

*Primary Examiner*—Kevin Shaver
*Assistant Examiner*—Michael B. Priddy
(74) *Attorney, Agent, or Firm*—Haynes and Boone, LLP

(57) ABSTRACT

The present invention is an alignment system by which a needle or other similar invasive device can be positioned for insertion so as to have a real-time, predetermined trajectory to a targeted tissue region, thereby reducing the need for repetitive needle insertion and withdrawal to move the tip of the instrument accurately to the target site.

13 Claims, 8 Drawing Sheets

PERCUTANEOUS NEEDLE ALIGNMENT SYSTEM AND ASSOCIATED METHOD

RELATED U.S. APPLICATION DATA

This application claims priority from U.S. Provisional Application Nos. 60/211,279 filed Jun. 13, 2000, and 60/216,378 filed Jul. 5, 2000, both incorporated herein by reference.

BACKGROUND OF THE INVENTION

1. Field of the Invention

The present invention generally relates to a trajectory system for medical instruments, and more particularly to a light-guided alignment system for a percutaneous needle.

2. Description of Related Art

Guidance methods are often used in conjunction with various injection procedures. The most common guidance method for inserting surgical instruments such as puncturing needles through the skin and to a subsurface injection site is simply reliance on the clinician's experience in visualizing a proper injection trajectory, and then maintaining that trajectory throughout insertion.

One type of injection procedure is the spinal injection, performed most often by a pain management specialist in which a mixture of steroid and anesthetic is delivered to specific internal structures of the body including, but not limited to, (i) a facet joint, (ii) an area surrounding a spinal nerve root, (iii) a major articulation, for example, a sacro iliac joint, and (iv) a vertebral disk space (IDET, discography). The purpose of these types of injections is to provide pain relief, as well as valuable diagnostic information for identifying pain generators.

Another procedure is the use of a needle to obtain a biopsy sample. One example of this procedure is the lumbar puncture. A lumbar puncture is a commonly performed diagnostic, yet rarely therapeutic, procedure. In a normal pressure hydrocephalus, a spinal needle is guided into a patient's body in order to remove cerebrospinal fluid for therapeutic purposes. The needle is passed into proximity of spinal cord.

Conventional guidance of the injection needle into the patient is performed free-hand and with visual guidance by the clinician performing the procedure. That is, the clinician estimates the proper injection trajectory of the needle through the skin and to a target site based on years of injection practice and training. While skilled clinicians may perform the insertion satisfactorily, a novice (or less experienced clinician) has difficulty obtaining the requisite skill.

Success in performing puncture procedures requires knowledge of the patient's anatomy and both good manual dexterity and eye-hand coordination. In the case of performing a spinal tap, there exists a steep learning curve, highly dependent on how many spinal taps the clinician has performed during training. Much to the detriment of the patient, puncture procedures such as the lumbar puncture commonly are performed in emergent situations, frequently by the most junior medical person on staff. If not in the case of an emergency, spinal injections are performed and practiced by medical students in teaching hospitals, wherein the student is under the supervision of a more experienced physician. In such settings, there are limited options for the mentor or teacher to convey to the trainee just what the intended trajectory should be based on the years of experience of the mentor. The mentor often is reluctant to "talk" the trainee through the procedure, as this can make the awake patient who is listening quite uncomfortable. Yet, this lack of oral communication often results in a miscalculated pass of the spinal needle by the trainee.

The free-hand, visual guidance approach to aligning spinal injections can be supplemented with fluoroscopic assistance in radiology suites or in the operating room where sophisticated imaging devices are available. The imaging device commonly available in the operating room involves uniplanar fluoroscopy provided by a "C-arm" imaging device. In computer tomography or fluoroscopically guided procedures, imaging is used to localize and determine the position of a subsurface target requiring treatment or medical investigation. Once the position of the subsurface target is determined, a clinician then uses the imaging equipment to select the desired path of access to the subsurface target with invasive instruments such as needles, drainage catheters, localization wires or other tools to perform necessary procedures. After the desired path is selected, the clinician guides the invasive instrument along the path to the target by maintaining the invasive instrument in alignment with that selected path.

The disadvantages of this type of needle guidance are apparent and well understood both by those in the art and those unfortunate patients that require repeated insertions with misguided needle insertions. The process of inserting the needle from an initial stage (prior to puncture when the needle point is resting on the patient's skin at the insertion site and in proper alignment as viewed by the clinician in the monitor) to a final stage (when the medication has been delivered to the target site) takes steady hands and repeated views back to the monitor to ensure the insertion trajectory is followed throughout the procedure. Even assuming this conventional needle guidance is successful in just one pass, repeated fluoroscopy is still necessary during the one pass, all the while exposing the patient to numerous doses of radiation.

The inability of the clinician to ensure, in real-time, the correct trajectory of the needle from the insertion site to the target site may cause significant patient discomfort. Even when guided by free-hand with C-arm assistance, the clinician typically must insert and withdraw the needle multiple times to reach a sufficient confidence level that the target site has be reached.

One technique used in overcoming a few of the disadvantages of fluoroscopically guided free-hand insertion of a needle is the use of a light beam serving as a visible guide for accessing the subsurface target with the needle, the needle being maintained in an aligned position with the light beam during insertion. Light emitting diodes "LEDs" are frequently used in medicine with percutaneous insertion of spinal needles or other instruments such as pedicle screws. Typically, the light emitted by the LEDs identifies for the clinician the needle point of entry on the patient's skin.

For example, U.S. Pat. No. 6,041,249 to Regn discloses a device for making a guide path for an instrument. A light source located on a rail of a computed tomography apparatus emits a light beam toward the patient. When the light beam, insertion site and the target site are aligned, a needle is placed in the path of the beam and inserted into the body. The angle of the needle is adjusted during insertion to maintain the light beam in contact with the top end of the needle.

Other applications are known utilizing LEDs, including U.S. Pat. No. 6,096,049 to McNeirney et al., to identify trajectories for the insertion instrument. However, these devices are not very efficient. The beam of light is used to indicate the spot on the patient's skin through which the needle will puncture. Yet, if the patient moves thereafter, the true insertion site moves as well, and the procedure for identifying the spot on the body must be administered again. Thus, with the McNeirney et al. system, when a patient moves, the technician then must reposition the C-arm so as to redefine a new point of entry on the skin to adjust for the patient's movement. Repositioning the C-arm repeatedly in response to patient movement can be so time consuming as to render the McNeirney et al. system impractical.

Another problem that can arise with free-hand needle insertion primarily is due to the flexibility inherent in puncture needles in view of a needle's small diameter relative to its length. Typically the clinician holds the needle from only the distal end (with the clinician fingers), the proximal end of the needle resting on the patient's skin. This leaves the length of the needle unsupported, thus facilitating needle deflection under the insertion force of the clinician's fingers. The needle will bend/deflect as force is applied to the distal end to commence needle insertion.

Injection procedures also suffer from the problem of insufficient needle point friction control at the insertion site on the skin when beginning the insertion procedure. Prior to insertion, and even slightly after insertion, the needle can easily swivel off trajectory. In an unaided needle procedure, an on-phase insertion will be completely dependent on the steadiness of the clinician's hands. Thus, repeatable on-phase insertions can not be guaranteed even with the same clinician.

Further, once the insertion site has been identified on the patient's skin, the needle point is rested on the skin site, and the distal end of the needle is brought into a proper trajectory prior to insertion. During this phase of needle positioning, if too much pressure is exerted on the skin by the proximal end of the needle, the needle will puncture the skin prior to aligning the needle. Yet, if too little contact is brought against the skin and proximal end of the needle, the needle point can float above the insertion site, making the alignment procedure more difficult.

In view of the foregoing limitations in the prior art, it would be desirable to provide an alignment system by which a needle or other similar invasive device could be positioned for insertion so as to have a real-time, predetermined trajectory to a targeted tissue region, thereby reducing the need for repetitive needle insertion and withdrawal to move the tip of the instrument accurately to the target site.

It also would be desirable to provide an alignment system that minimizes or eliminates the need for repositioning the fluoroscopic device in response to each and every patient movement.

It would further be desirable to provide an alignment system incorporating a needle driver supporting the needle in its proper trajectory, the driver limiting the amount of needle deflection during insertion.

It also would be beneficial to provide an alignment system that provides needle point friction control during the alignment phase of the needle.

It is believed the prior art neither teaches nor suggests an alignment system that combines the beneficial features of those identified. Accordingly, there is a need in the art for such a needle alignment system, and it is to the provision of such a system that the present invention is primarily directed.

BRIEF SUMMARY OF THE INVENTION

Briefly described, in a preferred form, the present invention is an alignment and guidance system for a puncture device used to deliver injection material such as medicine to a subsurface target region or site within a patient's body. Alternatively, the puncture device can be used to receive injection material, such as removing biopsy fluid, from the subsurface target site. The present alignment system provides a clinician with precise guidance for the puncture device.

The present alignment system comprises an insertion device, an energy source and a reflecting element. The insertion device preferably is a needle, however the alignment system can be used with other puncture devices such as pedicle screws, heat probes and other inserted instruments. The needle has a proximal end for puncturing the skin and a distal end. The distal end of the needle can include a hub.

The energy source preferably is a light source being, for example, a lightbulb or LED. Alternatively, the energy source can be a non-visible source coupled with a sound-emitting device to indicate on-phase alignment. The light source is housed in the hub at the distal end of the needle, aligned parallel to the radial axis of the needle, and shining in the direction away from the proximal end of the needle.

The reflecting element is capable of reflecting the light emanating from the distal end of the needle back onto the hub. Preferably, the reflecting element comprises a reflective piece of radiolucent material adhered to the undersurface of a C-arm. The reflective element lies in a perpendicular plane from the radial axis on the needle.

When the light source is energized, the clinician can visualize the spot of reflected light on the hub and note how far the needle is off optimal alignment. The clinician then swivels the injection element accordingly until the reflected light is aligned with the shined light. The needle can then be advanced along the optimal injection trajectory so long as the reflected light is kept on the hub of the needle.

A process for aligning a puncture device according to the present invention is also disclosed. A similar process can be used to retrieve biopsy material from a subsurface target region.

The present invention can further comprise a needle driver for supporting the length of the needle in a proper trajectory. The needle driver is designed to prevent bending of the needle. In such an embodiment, the energy source can be communicative with the driver, instead of the needle, and the driver properly aligned as previously discussed. Once the driver trajectory is equivalent with the injection trajectory, the needle can be passed through the needle driver, and the injection be assured of alignment. Alternatively, the needle driver can itself be advanced percutaneously in some insertion techniques.

While the energy source can produce a single beam of light, the energy source used with the needle driver can alternatively produce a ring of light such that the energy source does not impede the travel of the needle through the needle driver. Further, although the energy source can be located on the distal end of the insertion element or needle driver, the energy source may alternatively be located at other sites along the needle and driver. However, the light source is aligned parallel to the radial axis of the needle, and shone in the direction away from the proximal end of the needle.

The present invention can further include a method and apparatus for stabilizing the proximal end of the needle, or proximal end of the needle driver, against excessive movement both during the aligning procedure and during needle insertion.

There are many advantages of the present invention. The present invention limits the amount of time and effort to align the needle into the optimal injection trajectory, and limits the amount of punctures correspondingly decreasing the amount of infusion of local anesthetic. The present device is further advantageous as it can be used in conjunction with the injection of local anesthetic so the anesthetized areas of tissue are located in proximity to (the same path of) the injection trajectory. Additionally, by having a more accurate insertion of the needle there will be less risk of injuring nearby structures due to the incorrect passage of an instrument along an undesired trajectory.

The present device also decreases fluoroscopy time and simplifies the identification of the insertion site. For example, to identify the needle insertion point according to the present invention, a radio-opaque object such as a hemostat is moved across the patient's skin. When the tip of the radio-opaque instrument is positioned within the line determined by the anatomic structure of interest and the perpendicular axis of the undersurface of the C-arm, an eclipse forms on the monitor such that the anatomic structure of interest and the tip of the radio-opaque object appear superimposed. Assuming the clinician is then comfortable that the fluoroscopic image indicates a proper path, the clinician marks a spot on the skin surface under the tip of the radio-opaque instrument. If by accident the patient slightly moves, the marked spot remains on the patient's skin and in most circumstances will still illustrate the proper insertion point. The spot of entry may change slightly and can be easily remarked by moving a radio-opaque object. Yet, the clinician will not need to reposition the C-arm to have the light hit the new entry point as the light is shining from the needle. However, with prior art trajectory systems that utilize light shone on the patient to identify the insertion site, if the patient subsequently moves, then the C-arm and attending machinery must be realigned. This can be quite a common problem, since the patients are rarely heavily sedated to such an extent that they do not move.

Placing the light on the needle itself is a dramatic improvement over the prior art injection procedures that have a light on the x-ray source, or have a light at a distant source from the patient. Utilizing a light directed from the needle and reflecting back from the reflective surface on the x-ray machine also is beneficial. The light shining from the needle, to the reflecting surface, and back travels twice as far than if only shining from the machine. Thus, when the clinician views the reflection of the light back on the emitting instrument, the light has traveled twice as far and is twice as sensitive for alignment purposes. Additionally prior art devices are very expensive, cumbersome and are not cost effective or time efficient.

Further, prior art guidance devices provide the clinician only two discrete settings, on or off alignment. The present invention provides the clinician an almost infinite range of on or off alignment information so the clinician can make a quantitative judgment based on how close the reflected light is from the energy source from where it came.

The present invention limits excessive x-ray exposure to the patient. The clinician using the present invention directs the light at the C-arm and looks for the reflection back toward a sheath as the technician can adjust the machine or move the C-arm around until it is centered over the instrument itself. For example, this could be 30° to the oblique and 20° to the cephalad and the technician will move the machine until the light source is directed back at the energy source itself. This provides an advantage as less fluoroscopic pictures are taken and less fluoroscopy exposure is needed. Fluoroscopy machines will last longer and more importantly the clinician and others, as well as the patient, will receive less radiation exposure.

Additionally, it is important to have the insertion site and target site aligned in the center of the C-arm. This reduces parallax which can be a source of error. Parallax may cause the image visualized on the x-ray machine not to be actually representative of space and the target area. Also, images in the center of the screen are more accurate than are the images off to the side of the screen. Therefore, it is advantageous for the clinician to place the anatomic structure of interest in the center of the screen even though frequently many operators are satisfied with having the anatomic structure of interested located towards the periphery of the machine. With prior art devices, it is too time consuming to continually take fluoroscopic pictures until the anatomic structure of interest is in the center of the screen. However, if one is able to simply locate the anatomic structure of interest on the screen, one can mark the insertion site on the skin and the present invention will allow the clinician to place the insertion site in the center of the screen without taking anymore images simply by activating the light and directing it to the center of the undersurface of the C-arm. In this way the technician can simply move the machine until the light which is reflecting back at the present device hits the reflective surface in the very center of the undersurface of the C-arm or in the very center of the reflective surface.

The present invention need not necessarily be used with fluoroscopy, but can also be used as a teaching tool for lumbar punctures and other biopsy procedures. The lumbar puncture is often performed by third-year medical students and is based on known anatomy. With the present invention, the correct trajectory can be presented to the student by having a light on the end of the needle and watching and using this light as a reference point. For example, if a supervising physician in the room is aware of the correct trajectory based on his/her experience and knowledge and is trying to convey this to the medical student performing the injection of a needle, the present invention is a nice teaching tool to convey to the medical student the correct trajectory for insertion. Rather than using terms of "move the needle tip" or "move the needle hub right, left, up or down", the supervising physician can simply take hold of the needle without advancing it, and show the medical student the correct trajectory without advancing the needle and the medical student can take notice of where the light, which is added to the hub of the spinal needle, appears relative to a reference point within the room. In this way the medical student can pass the needle as the supervising physician intended the medical student to do by assuring that the student's light path shines upon the mark indicated by the supervisor.

These and other objects, features and advantages of the present invention will become more apparent upon reading the following specification in conjunction with the accompanying drawing figures.

DETAILED DESCRIPTION OF A PREFERRED EMBODIMENT

Figure 1:
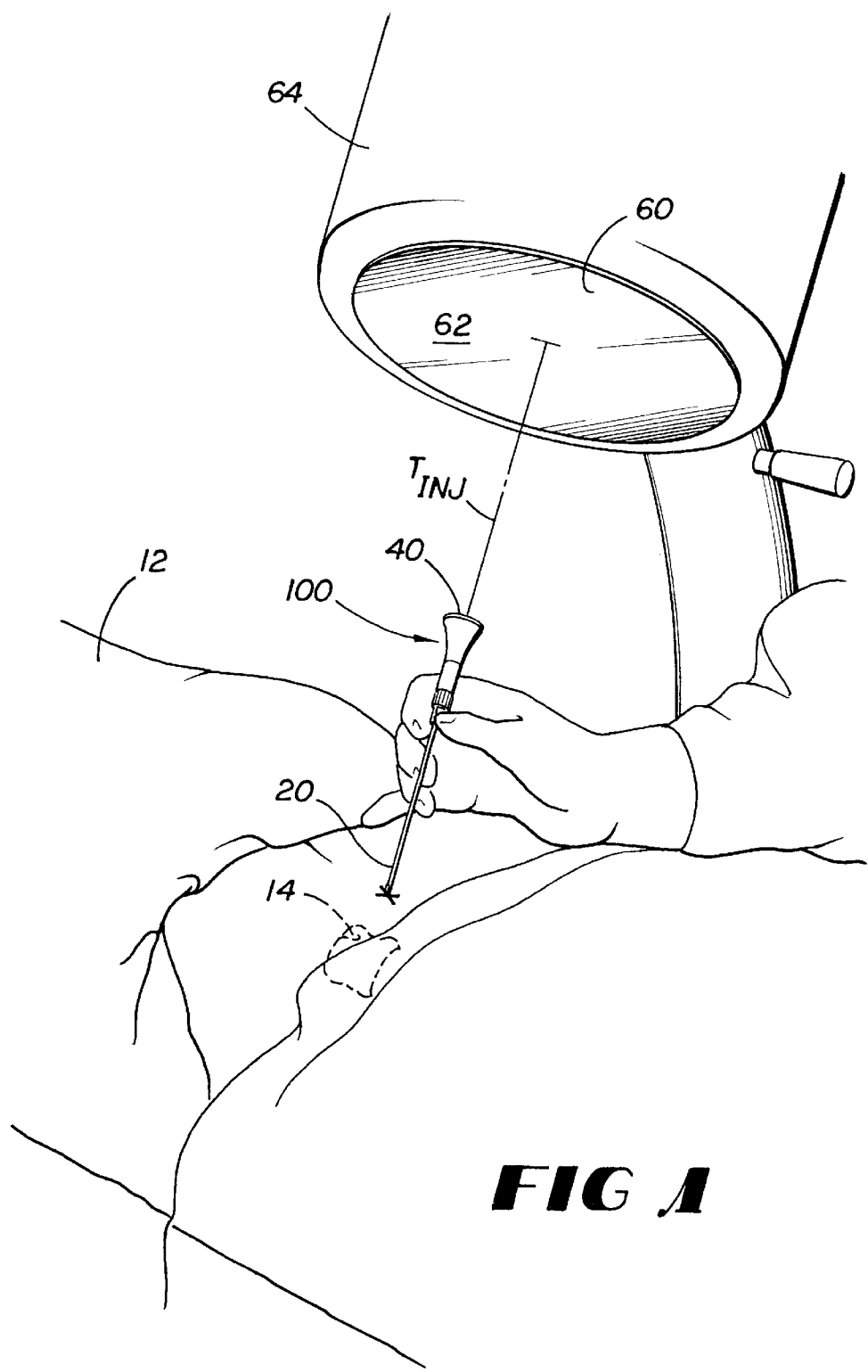
FIG. 1 illustrates a preferred embodiment of the present needle alignment system.

Referring now in detail to the drawing figures, wherein like reference numerals represent like parts throughout the several views, FIG. 1 illustrates the present alignment system 100 comprising a insertion device 20, an energy source 40 and a reflecting element 60. The alignment system 100 is located in an injection trajectory $T_{INJ}$ aligning an insertion site X on the skin of a patient 12, and a target site 14 below the skin.

Figure 2:
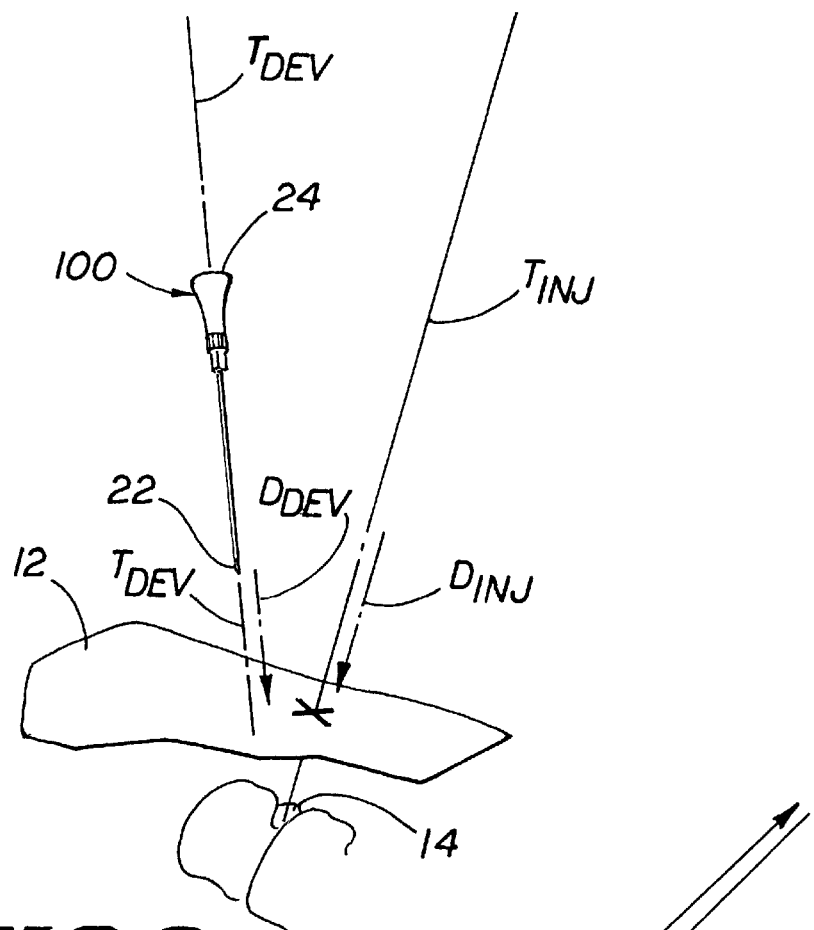
FIG. 2 is a schematic of the trajectories and directions referred to herein.

As shown in FIG. 2 and as used herein, the term "injection trajectory" $T_{INJ}$ is defined as the trajectory passing through the insertion site X on the skin and the target site 14 within the body, and the term "injection direction" $D_{INJ}$ is defined as the direction lying on the injection trajectory $T_{INJ}$ from the insertion site X to the target site 14.

As distinguished from the injection trajectory $T_{INJ}$ and the injection direction $D_{INJ}$, the insertion device 20 has a device trajectory $T_{DEV}$ (or sometimes needle trajectory) and a device direction $D_{DEV}$ (or sometimes needle direction). "Device trajectory" $T_{DEV}$ is defined as the trajectory of alignment of the proximal 22 and distal ends 24 of the insertion device 20, and the "device direction" $D_{DEV}$ is the direction lying on the device trajectory $T_{DEV}$ from the distal end 24 to the proximal end 22 of the insertion device 20. It will become apparent that the present invention preferably is used to position the device trajectory $T_{DEV}$ equivalent to the injection trajectory $T_{INJ}$.

Figure 3:
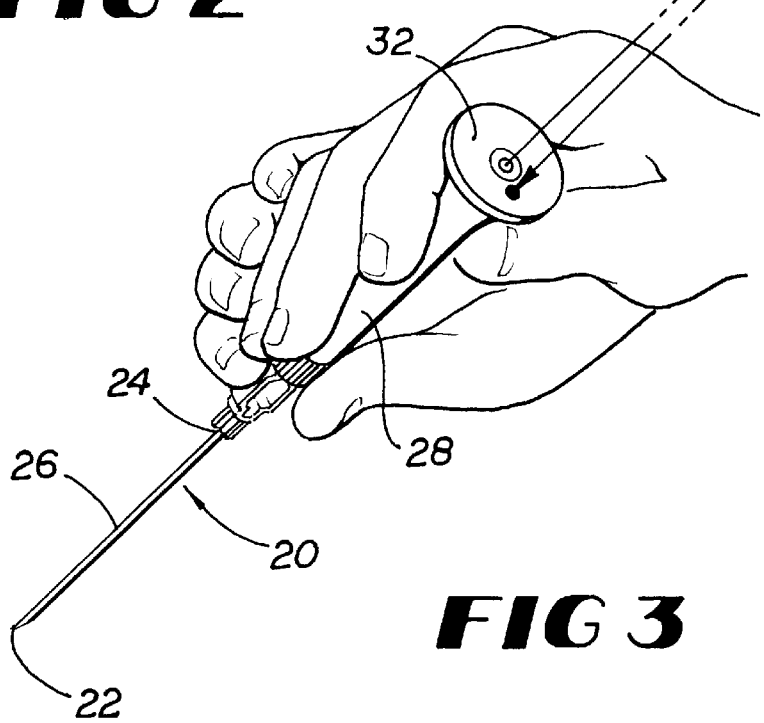
FIG. 3 shows a perspective view of the insertion device of the present invention.

The insertion device 20 illustrated in FIG. 3 comprises a needle 26 having a proximate puncture end 22, an energy source housing 28 located at the distal end 24, and a viewing surface or hub 32 located on the housing 28.

Figure 4:
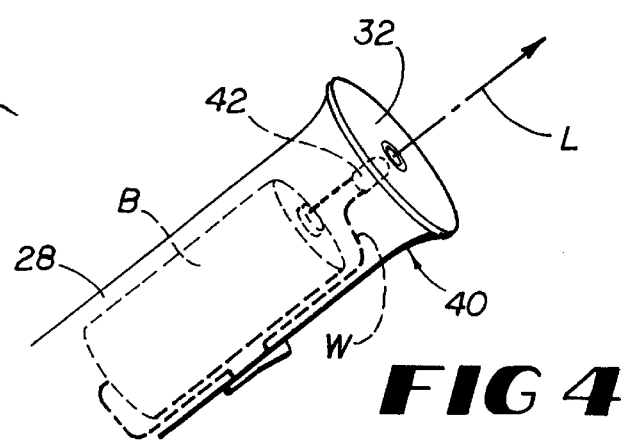
FIG. 4 is an interior view of the energy source housing of the present invention.

A light source 42 of the energy source 40 can be located within the energy source housing 28, the light source 42 being, for example, a small lightbulb connected by wires W to a battery B. FIG. 4. Alternatively, the light source 42 can comprise an LED. The energy source 40 is arranged such that that light L from the light source 42 is directed in an opposite direction than the prior-defined device direction $D_{DEV}$.

Figure 5:
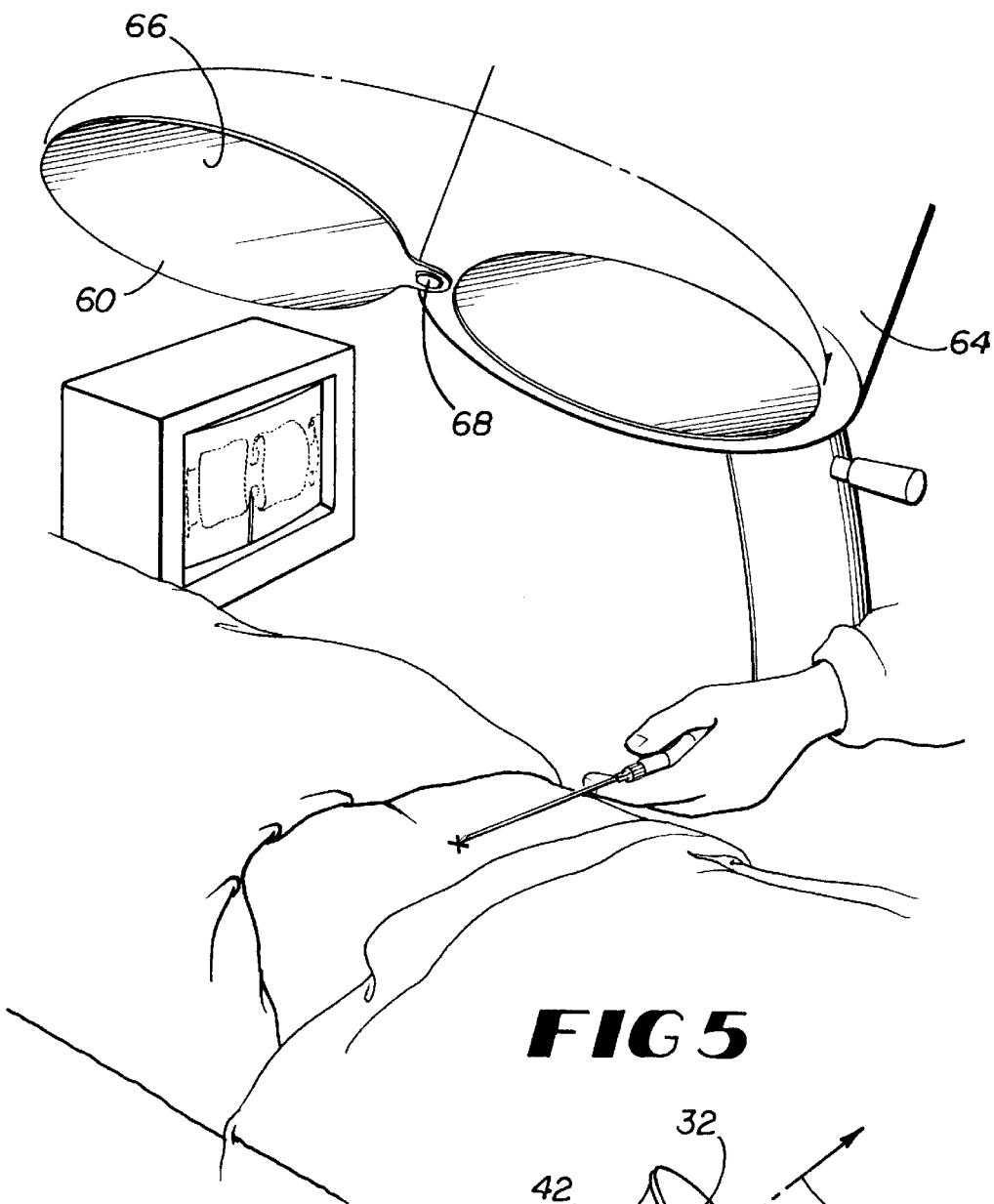
FIG. 5 illustrates one embodiment of the reflecting surface of the present invention.

The reflecting element 60 can comprise a reflective piece of radiolucent material 62 adhered to the undersurface of a C-arm 64, as shown in FIG. 1. Alternatively, the reflecting element 60 can comprise a swinging element 66 of radiolucent material pivotal about a pivot 68 such that the element 66 can easily located in proximity to the undersurface of the C-arm 64. FIG. 5. The reflecting element 60 should adhere/align with the undersurface of the C-arm 64 so that it is flat and flush with the undersurface of the C-arm 64.

Figure 6:
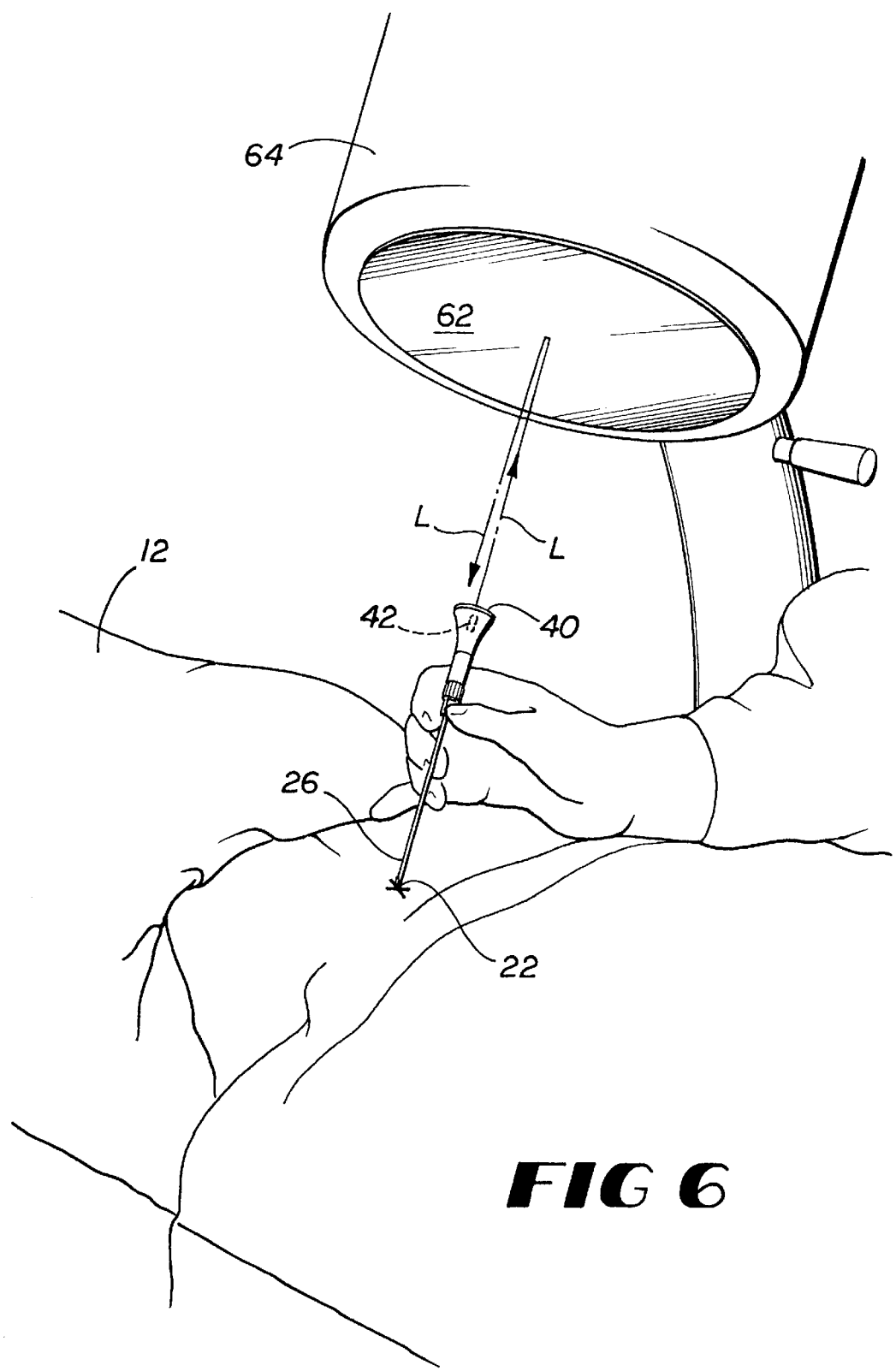
FIG. 6 shows an "on-phase" operation of the present invention.

FIG. 6 illustrates that with the puncture end 22 of the needle 26 in contact with the X mark, the light L from the energy source 40 shines upon and reflects away from the reflective covering 62 of the C-arm 64, which conventionally is a distance of about 1½ feet away from the patient 12. The light L is reflected back towards the light source 42, wherein surface 32 indicates whether the light L reflects directly back at the light source 42; thus ensuring proper needle alignment and an "on-phase" indication. The on-phase indication means the needle trajectory $T_{DEV}$ is equivalent to the injection trajectory $T_{INJ}$.

Figure 7:
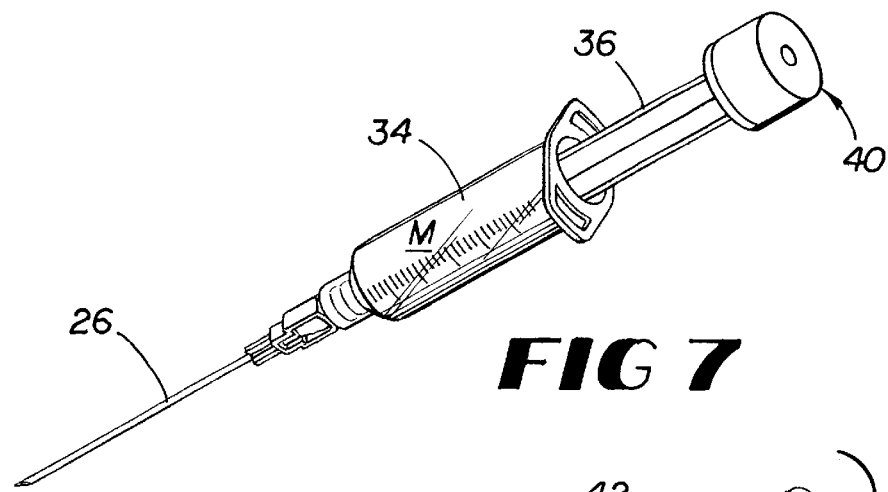
FIG. 7 is a perspective view of another preferred embodiment of the insertion device and energy source of the present invention.

Another embodiment of the combination of the insertion device 20 and energy source 40 of the present invention is shown in FIG. 7, wherein the insertion device 20 comprises a needle 26 in communication with an injection store 34 capable of storing injection material M for delivery to the target site 14. A plunger 36 of the insertion device 20 can include the energy source 40.

Figure 8:
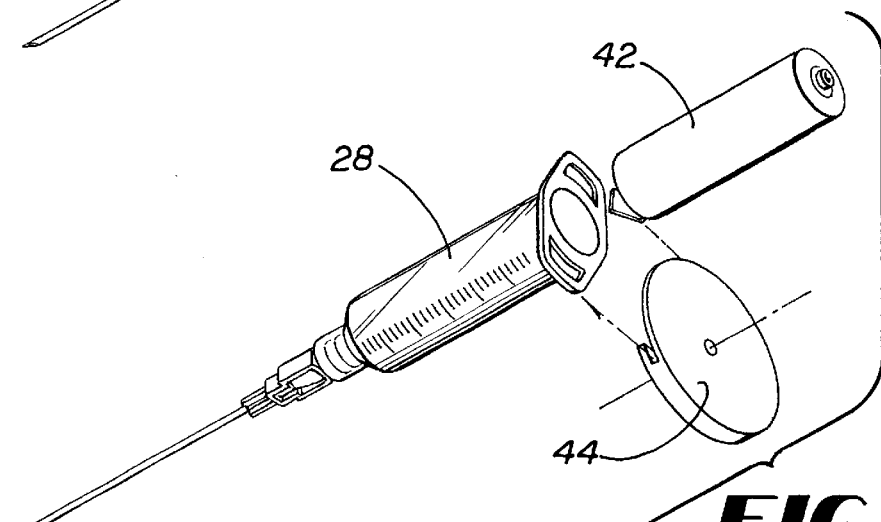
FIG. 8 is a perspective view of a reusable light source embodiment of the present invention.

Although the preferable construction of the present invention incorporates an energy source 40 that is of such expense that it can be thrown away after use; thus, enabling a fully disposable unit, FIG. 8 illustrates one example of a light source 40 being capable of numerous uses. A self-contained light source 42 can be slipped into an energy source housing 28 that is sealable and sterile, so that the removable light source 42 need not necessarily be sterile. The energy source housing 28 has a cover 44 that provides for such a reusable light source 42.

Figure 9:
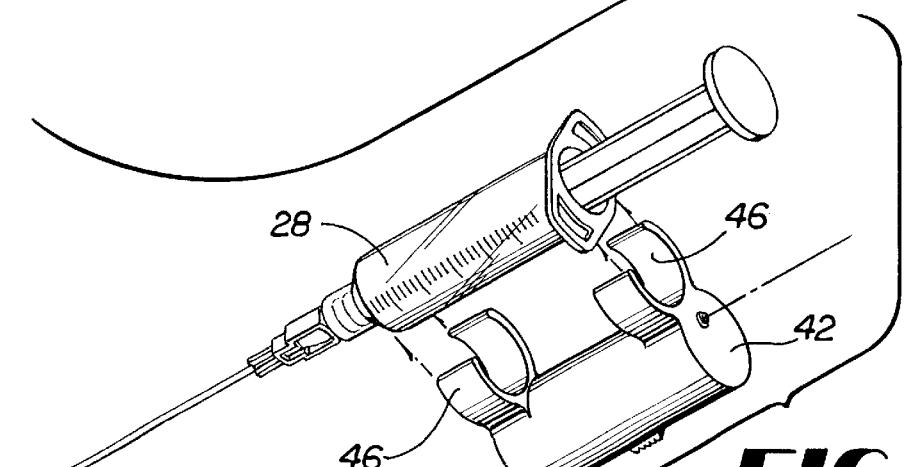
FIG. 9 is view of yet another preferred embodiment of the light source of the present invention.

FIG. 9 shows an alternate embodiment of the light source 42, wherein the light source 42 need not be located directly on the distal end 24 of the insertion device 20. Further, FIG. 9 illustrates that the light source 42 can be releasably secured to the insertion device, for example, via clips 46. In such an embodiment, it will be understood by those in the art that the light L shining from this embodiment of the light source 42 will have a have a trajectory parallel with that of the needle trajectory $T_{DEV}$.

Figure 10:
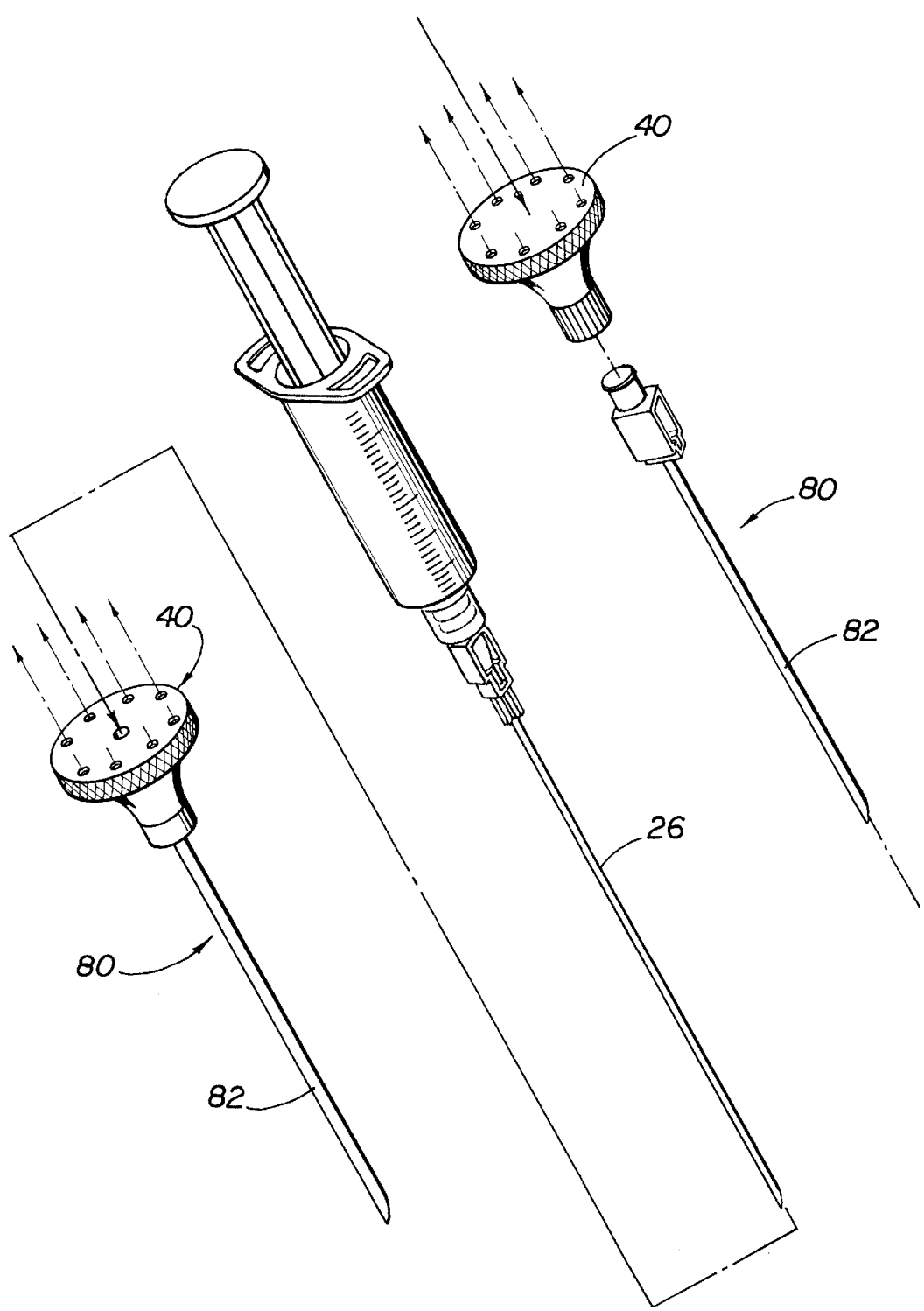
FIG. 10 is an exploded view of a needle driver of the present invention.

The present invention 100 can further comprises a needle driver 80 that includes the energy source 40, as shown in FIG. 10. The needle driver 80 comprises a tubular member 82 of sufficient strength and having an interior space which has a diameter slightly greater than the diameter of the needle 26, such that the needle 26 can slip within the tubular member 82. The needle driver 80 supports the length of the needle in a proper trajectory, and is designed to prevent bending of the needle 26. The energy source 40 as shown can be communicative with the needle driver 82, instead of the needle 26, and the driver 82 itself aligned. Once the driver 82 is aligned equivalent with the injection trajectory $T_{INJ}$, the needle 26 can be passed through the needle driver 82, and the injection be assured of alignment. Alternatively, the needle driver 82 can itself be advanced percutaneously in some insertion techniques. As shown in this embodiment, while the energy source 40 can produce a single beam of light L, the energy source 40 can alternatively produce a plurality of beams, for example a ring of light, such that the energy source 40 does not impede the insertion and travel of the needle 26 through the needle driver 80.

Figure 11:
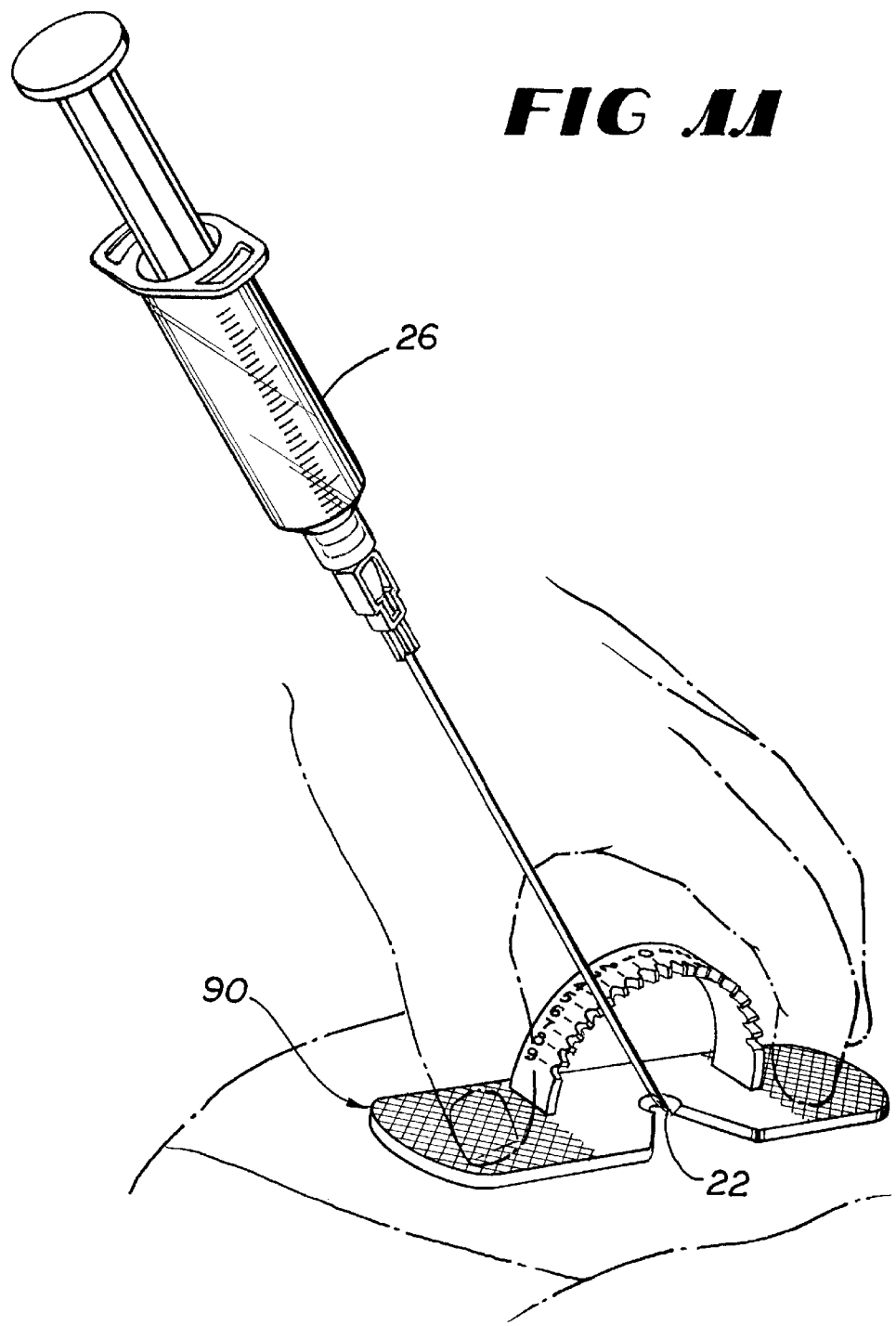
FIG. 11 illustrates a stabilizing element according to a preferred embodiment of the present invention.

The present invention can further comprise a stabilizing element 90, shown in FIG. 11. The stabilizing element 90 is designed to restrain the proximal end 22 of the needle 26, or proximal end of the needle driver 80, against excessive movement both during the aligning procedure and during needle insertion. This needle point friction control can be delivered by a stabilizing element 90 in contact with the skin, which stabilizing element 90 maintains the proximal end of the needle sufficiently away from the skin to prevent a mistaken injection, but close enough so that when proper alignment is established, the needle can easily be injected into the insertion site at the insertion trajectory. The stabilizing element also ensures that the needle does not easily swivel off trajectory regardless of the steadiness of the clinician's hands.

The stabilizing element 90 can incorporate indicia representative of differing trajectories. Alternatively, the stabilizing element 90 can be composed of a malleable radiolucent putty which can form fit to the subjects skin contour.

Alignment Procedure

Figure 12:
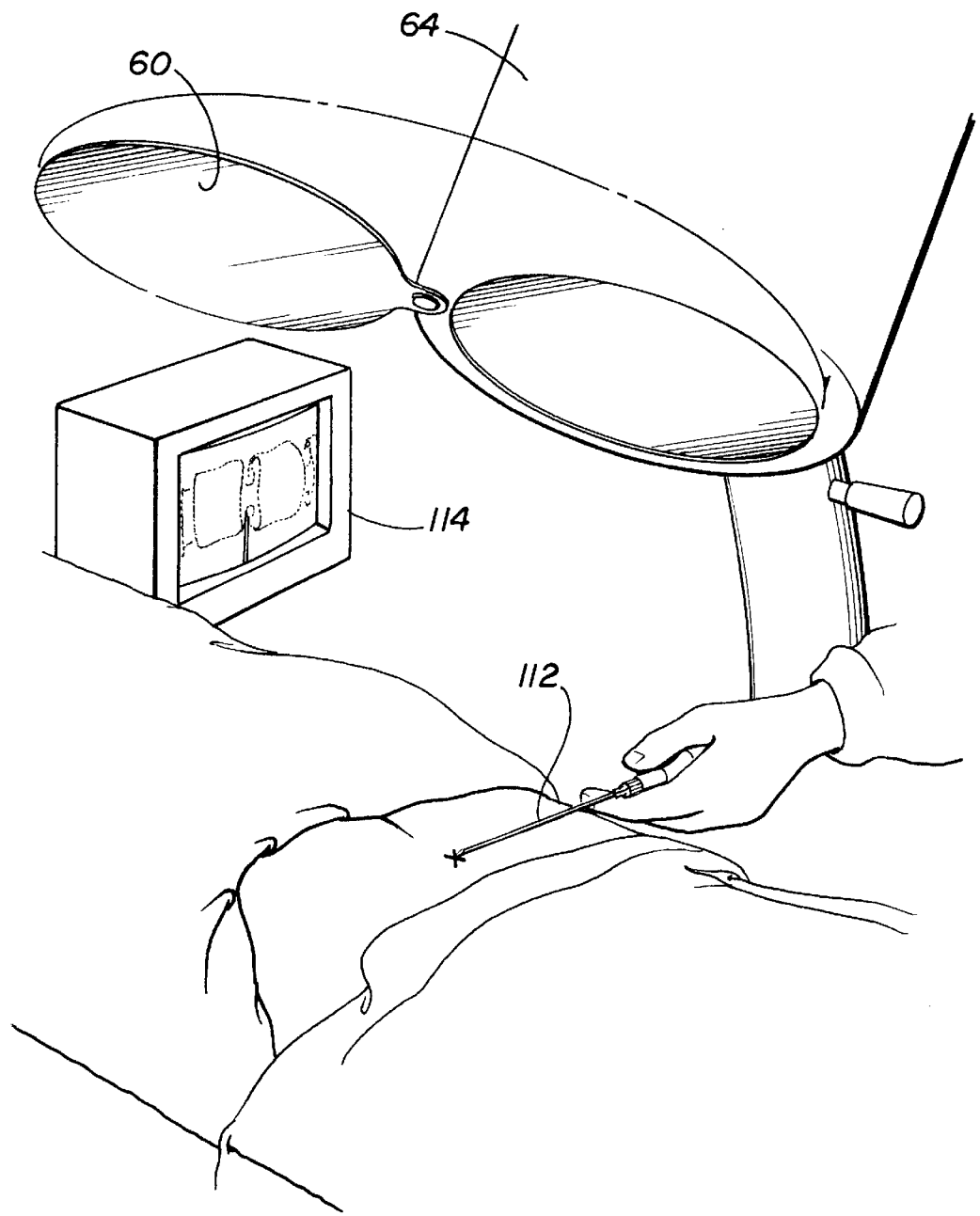
FIG. 12 illustrates one way to mark the insertion site on a patient.

For a spinal injection, the patient typically is positioned to lie face down. The C-arm 64 fluoroscopic machine is moved about the patient 12 until the clinician has visualized both a skin puncture site for the needle (the insertion site X), and an internal anatomic body structure (the target site 14), to receive the injected medication. As illustrated in FIG. 12, the clinician positions the reflective element 60 of radiolucent material to the undersurface of a C-arm 64. The C-arm 64 can then be initially positioned by the technician by centering the target site 14 with the center of the undersurface of the C-arm 64. Then, to identify the insertion site X, the clinician moves a radio-opaque object 112 (such as a hemostat or scissors) on the skin surface while watching a real time x-ray image on the fluoroscopic monitor 114. For optimal alignment, the C-arm 64 is positioned so the anatomic structure of interest 14 is visualized in the center of the image recorded. The C-arm 64 and the radio-opaque object 112 are moved iteratively until the fluoroscopic image indicates that the tip of the radio-opaque object 112 is aligned with the subsurface target site 14. The C-arm can be rotated either obliquely (side to side), or cephalad (toward the head), or caudad (toward the feet).

When the image illustrates that the tip of the radio-opaque object 112 is aligned with the subsurface target site 14, the undersurface of the C-arm 64 lies in a plane normal to the injection trajectory $T_{INJ}$. Once the injection trajectory $T_{INJ}$ has been determined through the positioning of the C-arm 64, the C-arm 64 is locked against changing its orientation, thereby resulting in an effective memorization of the injection trajectory $T_{INJ}$.

The insertion site X is marked on patient at that location where the tip of the object 112 is aligned in the monitor 114 with the subsurface target site 14. The clinician then places the proximal end 22 of the needle 26 on the desired marked skin site X, and energizes the light source 42 on the distal end 24 of the needle 26 so as to produce a beam of light L in the device trajectory $T_{DEV}$ and shining in the opposite direction of the device direction $D_{DEV}$. The light path L reflects from the radiolucent material 62 back down toward the patient. The clinician moves the distal end 24 of the needle 26 until the reflective path of light shines back against the energy source 40. The clinician can continually view the reflected light in the hub 32 and readjust the position of the hub 32 until the reflected light and the shone light interfere with one another. At this instance, the device trajectory $T_{DEV}$ is spatially aligned and equivalent with the injection trajectory $T_{INJ}$, and the procedure can begin.

When this "on-phase" alignment occurs, the clinician punctures the skin and advances the spinal needle 26 into the patient 12 and can be confident that the advancing needle 26 remains in a trajectory which is in line with the path predetermined by the x-ray image or "on phase". It may be necessary to puncture the skin minimally and then establish "on-phase" position before further advancing into the deeper and denser (less forgiving) tissues.

When an x-ray is taken and shown in the fluoroscopic monitor 114, and the clinician has successfully aligned the present invention 100, a "hubogram" will appear in the monitor 114. The term hubogram is the optimal fluoroscopic image of a spinal needle 26 that has been advanced perfectly "on phase". This hubogram will look like a small dot or will look like a picture of the hub 32 (or that portion of the present invention which is radio-opaque). If the device trajectory is off by just a few degrees of the injection trajectory, the size of the dot in the image will grow.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. An insertion device trajectory system, comprising:
   an insertion device located a distance from a reflecting element; and
   an energy source for production of an energy path in a direction toward the reflecting element and away from the insertion device; wherein the reflecting element reflects the energy path toward the energy source thereby indicating any trajectory correction required for the insertion device.

2. A percutaneous instrument trajectory system comprising:
   (a) a percutaneous instrument located a distance from a first surface;
   (b) an energy source for production of an energy path in a direction toward the first surface and away from the percutaneous instrument; and
   (c) a reflecting element in communication with the first surface, the reflecting element for reflecting the energy path toward the energy source;
   the proximity of the reflected energy path to the energy source indicating any trajectory correction required for the percutaneous instrument.

3. The trajectory system of claim 2 further comprising an indication surface for indicating the location of the energy path upon reflection from the reflecting element.

4. The trajectory system of claim 3 further comprising an instrument driver through which the instrument can be inserted.

5. The trajectory system of claim 3 further comprising a stabilizing element for guiding the instrument.

6. The trajectory system of claim 3, the energy source including a visible light source.

7. The trajectory system of claim 6, the first surface being a surface of a radio-imaging device and the reflecting element being radiolucent material.

8. A percutaneous needle alignment system for use with a patient having a subsurface target site, the target site reachable within the patient through an injection trajectory, the alignment system comprising:
   an insertion device located between a patient and a first surface, the insertion device having a proximal end and a distal end, the insertion device being in a device trajectory, the proximal end of the insertion device for insertion into a patient and reaching a subsurface target site;
   a reflecting element in communication with the first surface; and a light source located on the distal end of the insertion device for production of a light path in a direction toward the reflecting element, the light path reflectable off the reflecting element and toward the light source;

wherein the proximity of the reflected light path to the light source indicates any trajectory correction required for the instrument.

9. The alignment system of claim 8 further comprising a viewing surface for continually indicating the location of the reflected light path, the location of the reflected light path on the viewing surface relating to the difference between the injection trajectory and the device trajectory, the insertion device movable such that the injection trajectory and the device trajectory are substantially similar.

10. The alignment system of claim 9 further comprising a needle driver defining an interior space having a diameter slightly greater than a diameter of the insertion device such that the needle device can slip within the needle driver.

11. A method of aligning a percutaneous device for use with a patient having a subsurface target site, the target site reachable within the patient through an insertion site at an injection trajectory, the method of aligning the instrument comprising the steps of:

aligning the percutaneous device into a device trajectory, during which time the device is distal an insertion site on the patient;

generating an energy path from an energy source located on the percutaneous device;

reflecting the energy path such that the proximity of the reflected energy path to the energy source indicates the amount of realignment necessary for the percutaneous device such that the device trajectory will approximately equal the injection trajectory; and realigning the percutaneous device such that the device trajectory approximately equals the injection trajectory.

12. The method of aligning the percutaneous instrument according to claim 11, the energy path emanating from the energy source in a direction generally opposite the direction from the device to the insertion site.

13. The method of aligning the percutaneous instrument according to claim 11, further comprising the step of inserting the percutaneous device through a needle driver.

* * * * *